(12) United States Patent
Li et al.

(10) Patent No.: US 10,032,988 B2
(45) Date of Patent: Jul. 24, 2018

(54) ANTHRACENE-CONTAINING DERIVATIVE, PRODUCTION PROCESS THEREOF AND ORGANIC ELECTROLUMINESCENT DISPLAY DEVICE

(71) Applicants: Boe Technology Group Co., Ltd., Beijing (CN); JiLin OLED Material Tech Co., Ltd., Changchun (CN)

(72) Inventors: Na Li, Beijing (CN); Xiaoyu Ma, Beijing (CN); Hui Wang, Beijing (CN); Lujiang Huangfu, Beijing (CN)

(73) Assignees: BOE TECHNOLOGY GROUP CO., LTD., Beijing (CN); JILIN OLED MATERIAL TECH CO., LTD., Changchun (CN)

( * ) Notice: Subject to any disclaimer, the term of this patent is extended or adjusted under 35 U.S.C. 154(b) by 331 days.

(21) Appl. No.: 14/418,244

(22) PCT Filed: May 27, 2014

(86) PCT No.: PCT/CN2014/078520
§ 371 (c)(1),
(2) Date: Oct. 20, 2015

(87) PCT Pub. No.: WO2015/085720
PCT Pub. Date: Jun. 18, 2015

(65) Prior Publication Data
US 2016/0064668 A1    Mar. 3, 2016

(30) Foreign Application Priority Data
Dec. 10, 2013    (CN) .......................... 2013 1 0670443

(51) Int. Cl.
C07C 211/31    (2006.01)
H01L 51/00    (2006.01)
(Continued)

(52) U.S. Cl.
CPC ............ *H01L 51/006* (2013.01); *C07C 45/59* (2013.01); *C07C 46/00* (2013.01); *C07C 51/00* (2013.01);
(Continued)

(58) Field of Classification Search
None
See application file for complete search history.

(56) References Cited

FOREIGN PATENT DOCUMENTS

| CN | 103173211 A | 6/2013 |
| CN | 103187531 A | 7/2013 |

(Continued)

OTHER PUBLICATIONS

Search Report and Written Opinion from PCT/CN2014/078520, dated Sep. 1, 2014.

*Primary Examiner* — Gregory D Clark
(74) *Attorney, Agent, or Firm* — Westman, Champlin & Koehler, P.A.

(57) ABSTRACT

The invention discloses an anthracene-containing derivative, the production process thereof and an organic electroluminescent display device, wherein the anthracene-containing derivative has a general molecular structural formula of Formula I, wherein, $R_1$ group is selected from an aromatic group or a fused aromatic group having a carbon atom number of 6 to 18, $R_2$ group is selected from an amine group. By using the above described anthracene-containing derivative as a green phosphorescent host material, a green fluorescent host material, a hole injection material, or a hole transporting material in an organic electroluminescent display device, the light emitting efficiency and the light emitting brightness of the organic electroluminescent display device may be improved.

10 Claims, 3 Drawing Sheets

(51) Int. Cl.
*C09K 11/06* (2006.01)
*C07C 211/61* (2006.01)
*C07C 45/59* (2006.01)
*C07C 46/00* (2006.01)
*C07C 51/00* (2006.01)
*C09K 11/02* (2006.01)
*H01L 51/50* (2006.01)

(52) U.S. Cl.
CPC .......... *C07C 211/61* (2013.01); *C09K 11/025* (2013.01); *C09K 11/06* (2013.01); *H01L 51/0055* (2013.01); *H01L 51/0058* (2013.01); *C07C 2603/26* (2017.05); *C07C 2603/52* (2017.05); *C09K 2211/1007* (2013.01); *C09K 2211/1011* (2013.01); *C09K 2211/1014* (2013.01); *H01L 51/5012* (2013.01); *H01L 51/5016* (2013.01); *H01L 51/5088* (2013.01)

(56) References Cited

FOREIGN PATENT DOCUMENTS

| | | | | |
|---|---|---|---|---|
| CN | 103664648 A | 3/2014 | | |
| KR | 10-2012-0117694 | * 10/2012 | ............. | C07C 13/62 |
| KR | 2012-0117694 A | 10/2012 | | |

* cited by examiner

ANTHRACENE-CONTAINING DERIVATIVE, PRODUCTION PROCESS THEREOF AND ORGANIC ELECTROLUMINESCENT DISPLAY DEVICE

CROSS-REFERENCE TO RELATED APPLICATION

This Application is a Section 371 National Stage Application of International Application No. PCT/CN2014/078520, filed 27 May 2014, which has not yet published, which claims priority to Chinese Application No. 201310670443.7, filed Dec. 10, 2013, in Chinese, the contents of which are hereby incorporated by reference in their entirety.

FIELD OF THE INVENTION

The invention relates to the technical field of display, especially relates to an anthracene-containing derivative, the production process thereof, and an organic electroluminescent display device.

BACKGROUND OF THE INVENTION

At present, comparing the organic electroluminescent display device (OLED) with the traditional liquid crystal display device (LCD), because of having the features such as fast response, large color field, extremely thin, realization of flexibility, and the like, OLED has gradually become the mainstream of the display field.

The basic structure of an OLED display device comprises a base substrate, an organic electroluminescent element formed on the base substrate; wherein each organic electroluminescent element comprises a cathode and an anode provided opposite to each other, and an organic light emitting layer between the cathode and the anode. The light emission of an OLED display device is achieved by applying a voltage between the anode and the cathode, wherein holes in the anode and electrons in the cathode recombine in the organic light emitting layer to form excitons, the excitons in excited state transfer into the ground state, so as to excite the organic light emitting material in the organic light emitting layer to emit light. The organic light emitting material may be divided into two types according to the light emitting mechanism: one is composed of a fluorescence material emitting light by singlet excitons, and the other is composed of a phosphorescent material emitting light by triplet excitons.

In an OLED display device, in order to improve the light emitting efficiency and the stability of the formed OLED, the organic light emitting layer may comprise film layers such as a hole injection layer, a hole transporting layer, a light emitting layer, an electron transporting layer, and an electron injection layer, and the like formed from different organic materials, respectively. In order to improve the light emitting efficiency of the organic light emitting layer, a doping material having higher quantum yield than that of the host material may be doped into the host material of the light emitting layer. This is because the excitons in excited state have the tendency of transferring the energy thereof to the material having a smaller band gap in the material near the recombination portion. Therefore, the doping material is selected from the materials having a higher quantum yield and a smaller band gap (larger wavelength) comparing with those of the host material; otherwise, the energy of the excitons in excited state will transfer to the host material having a lower quantum yield, so as to produce weak emission or no emission.

In order to improve the light emitting efficiency and the light emitting brightness of the organic light emitting layer in an OLED display device, it has become a problem to be solved by a person skilled in the art to provide a stable and highly efficient organic light emitting material to be applied into the organic light emitting layer of the OLED display device.

SUMMARY OF THE INVENTION

The examples of the invention provide an anthracene-containing derivative, the production process thereof and an organic electroluminescent display device, for improving the light emitting brightness and the light emitting efficiency of an OLED display device.

The examples of the invention provide an anthracene-containing derivative, which is used as a green phosphorescent host material, a green fluorescent host material, a hole injection material, or a hole transporting material in an organic electroluminescent display device, wherein the anthracene-containing derivative has a general molecular structural formula of:

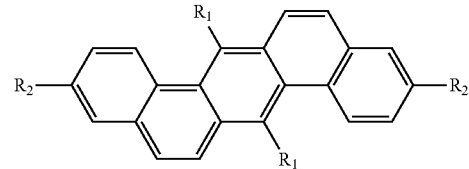

wherein $R_1$ group is selected from an aromatic group or a fused aromatic group having a carbon atom number of 6 to 18, and $R_2$ group is selected from an amine group, for example, an aromatic amine group, such as an aromatic amine group having a carbon atom number of 6 to 30.

The examples of the invention provide the above described anthracene-containing derivative. From the test results it can be known that, by employing the above described anthracene-containing derivative as the green phosphorescent host material, the green fluorescent host material, the hole injection material, or the hole transporting material in the organic electroluminescent display device, the light emitting efficiency and light emitting brightness in an organic electroluminescent display device may be improved.

Preferably, in the above described anthracene-containing derivative provided by the examples of the invention, the $R_1$ group is phenyl, 9-phenanthryl, p-tolyl, 4-biphenyl, or 2-naphthyl.

Preferably, in the above described anthracene-containing derivative provided by the examples of the invention, the $R_2$ group is diphenylamino, N-phenyl-4-biphenylamino, di(4-biphenyl)amino, N-phenyl-2-naphthylamino, 2,2-dinaphthylamino, or N-phenyl-3,5-diphenyl phenylamino.

The examples of the invention provide a production process suitable for any one of the above described anthracene-containing derivative, comprising the steps of:

under a protection gas atmosphere, adding a dibenzoanthracene bromide containing a $R_1$ group, an amine compound, sodium tert-butoxide, palladium acetate and a first organic solvent into a first reaction vessel, and continuously stirring the solution in the first reaction vessel; wherein the $R_1$ group is selected from an aromatic group or a fused aromatic group having a carbon atom number of 6 to 18;

adding tri-tert-butyl phosphine into the first reaction vessel dropwise, and heating to reflux such that the reactant is sufficiently reacted, and cooling to room temperature;

after a post-treatment (for example extracting, washing and drying), obtaining an anthracene-containing derivative.

Preferably, in the above production process provided by the examples of the invention, the first organic solvent is toluene.

Preferably, in the above production process provided by the examples of the invention, the dibenzoanthracene bromide containing a $R_1$ group is produced by the steps of: adding 1.2,5.6-di(2-bromo)benzo(9,10-dicarbonyl)anthracene and a second organic solvent into a second reaction vessel;

after 1.2,5.6-di(2-bromo)benzo(9,10-dicarbonyl)anthracene is dissolved into the second organic solvent, reducing the temperature of the second reaction vessel; adding butyl lithium into the second reaction vessel dropwise; after the reactant is sufficiently reacted, adding a solution of an iodide having a $R_1$ group into the second reaction vessel; raising the temperature of the second reaction vessel to normal temperature, such that the reactants are sufficiently reacted;

after a post-treatment, for example, extracting, washing, and drying, obtaining an alcohol of a dibenzoanthracene bromide containing a $R_1$ group;

adding the alcohol of the dibenzoanthracene bromide containing a $R_1$ group, potassium iodide, sodium dihydrogen phosphate and a third organic solvent into a third reaction vessel; heating to reflux such that the reactant is sufficiently reacted; and cooling to room temperature;

upon a post-treatment, for example, washing, filtering, and drying, obtaining the dibenzoanthracene bromide containing a $R_1$ group.

Preferably, in the above production process provided by the examples of the invention, the second organic solvent is tetrahydrofuran.

Preferably, in the above production process provided by the examples of the invention, the third organic solvent is glacial acetic acid.

Preferably, in the above production process provided by the examples of the invention, the 1.2,5.6-di(2-bromo)benzo(9,10-dicarbonyl)anthracene is produced by the steps of:

adding 7-bromonaphthofuran-1,3-dione and 2-iodonaphthalene into a fourth reaction vessel and heating the fourth reaction vessel;

adding aluminium trichloride into the fourth reaction vessel; performing reaction until no more hydrogen chloride is discharged; when the fourth reaction vessel is cooled, slowly pouring the solution in the fourth reaction vessel into an ice water solution of sodium hydroxide; removing the unreacted 2-iodonaphthalene by distillation; upon purification by filtering, obtaining a (6-bromo-1-(6-bromo-2-naphthoyl)-2-naphthoyl)aluminum dichloride; adding the (6-bromo-1-(6-bromo-2-naphthoyl)-2-naphthoyl)aluminum dichloride and concentrated sulfuric acid into a fifth reaction vessel; heating the fifth reaction vessel such that the reactants are sufficiently reacted, then cooling to room temperature; pouring the solution in the fifth reaction vessel into ice water; upon a post-treatment, for example, filtering, washing and, drying, obtaining the 1.2,5.6-di(2-bromo)benzo(9,10-dicarbonyl)anthracene.

Examples of the invention provide an organic electroluminescent display device, comprising: a base substrate, an organic electroluminescent element provided on the base substrate; wherein the organic electroluminescent element comprises: an anode and a cathode provided opposite to each other, and an organic light emitting material provided between the anode and the cathode;

At least one of the green phosphorescent host material, the green fluorescent host material, the hole injection material, or the hole transporting material in the organic light emitting material is any one of the above described anthracene-containing derivative provided by examples of the invention.

Examples of the invention provide the above described organic electroluminescent display device. Because at least one of the green phosphorescent host material, the green fluorescent host material, the hole injection material, or the hole transporting material in the organic light emitting material is an anthracene-containing derivative, from the test results it can be known that, the light emitting efficiency and the light emitting brightness of this organic electroluminescent display device are both improved.

DETAILED DESCRIPTION OF THE INVENTION

Figure 1:
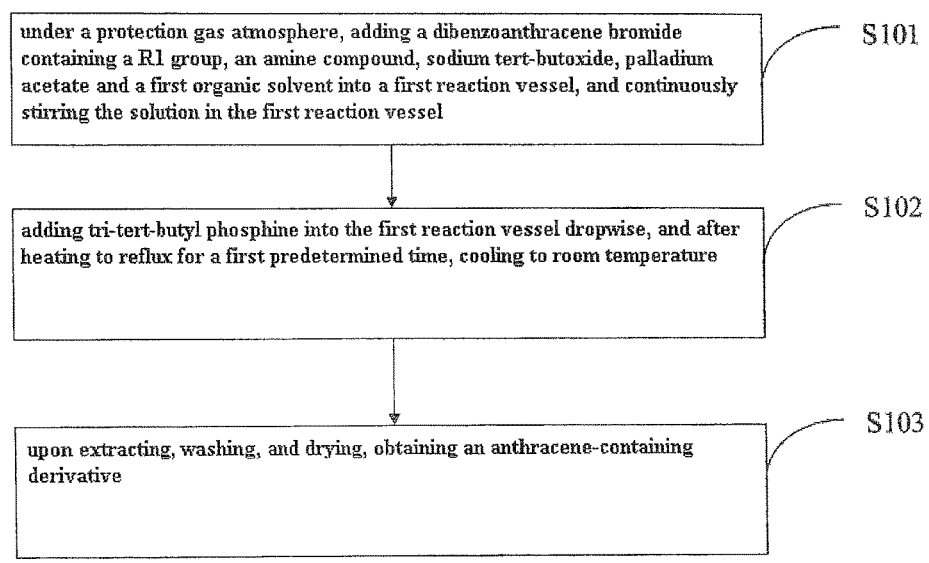
FIG. 1 is a flow chart of the production process of an anthracene-containing derivative provided by examples of the invention.

Specific embodiments of the anthracene-containing derivative, the production process thereof, and the organic electroluminescent display device provide by examples of the invention are described in details below with reference to Figures.

The examples of the invention provide an anthracene-containing derivative, which is used as a green phosphorescent host material, a green fluorescent host material, a hole injection material or a hole transporting material in an organic electroluminescent display device, wherein the anthracene-containing derivative has a general molecular structural formula of:

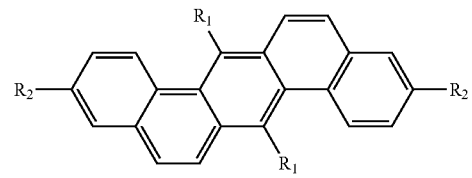

wherein $R_1$ group is selected from an aromatic group or a fused aromatic group having a carbon atom number of 6 to 18, and $R_2$ group is selected from an amine group.

The examples of the invention provide the above described anthracene-containing derivative. From the test results it can be known that, by employing the above described anthracene-containing derivative as the green phosphorescent host material, the green fluorescent host material, the hole injection material, or the hole transporting material in the organic electroluminescent display device, the light emitting efficiency and light emitting brightness in an organic electroluminescent display device may be improved.

Specifically, in the above described anthracene-containing derivative provided by examples of the invention, the $R_1$ group may specifically be phenyl, 9-phenanthryl, p-tolyl, 4-biphenyl, or 2-naphthyl.

Specifically, in the above described anthracene-containing derivative provided by examples of the invention, $R_2$ group may specifically be diphenylamino, N-phenyl-4-biphenylamino, di(4-biphenyl)amino, N-phenyl-2-naphthylamino, 2,2-dinaphthylamino, or N-phenyl-3,5-diphenyl phenylamino.

Furthermore, in the above described anthracene-containing derivative provided by examples of the invention, 30 types of anthracene-containing derivatives may be obtained by combining $R_1$ group and $R_2$ group. Specifically, the chemical structure formulas of the 30 types of anthracene-containing derivatives are as shown by the following Table 1.

TABLE 1

| Anthracene-containing derivative No. | Chemical structural formula of the anthracene-containing derivative |
|---|---|
| 1 | |
| 2 | |
| 3 | |

TABLE 1-continued
| Anthracene-containing derivative No. | Chemical structural formula of the anthracene-containing derivative |
|---|---|
| 4 | 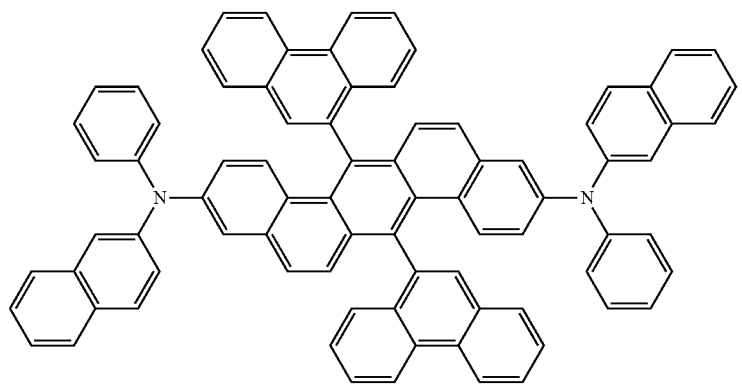 [SMILES: c1ccc(N(c2ccc3ccccc3c2)c2ccc3c(ccc4c(-c5cc6ccccc6c6ccccc56)c5c(ccc6cc(N(c7ccccc7)c7ccc8ccccc8c7)ccc65)c(-c5cc6ccccc6c6ccccc56)c43)c2)cc1] |
| 5 | 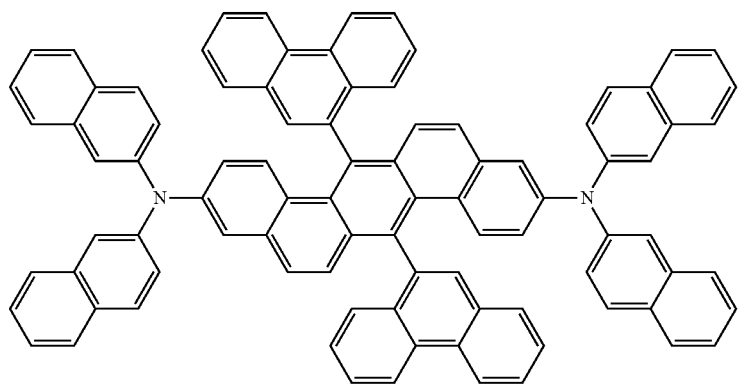 [SMILES: c1ccc2cc(N(c3ccc4ccccc4c3)c3ccc4c(ccc5c(-c6cc7ccccc7c7ccccc67)c6c(ccc7cc(N(c8ccc9ccccc9c8)c8ccc9ccccc9c8)ccc76)c(-c6cc7ccccc7c7ccccc67)c54)c3)ccc2c1] |
| 6 | 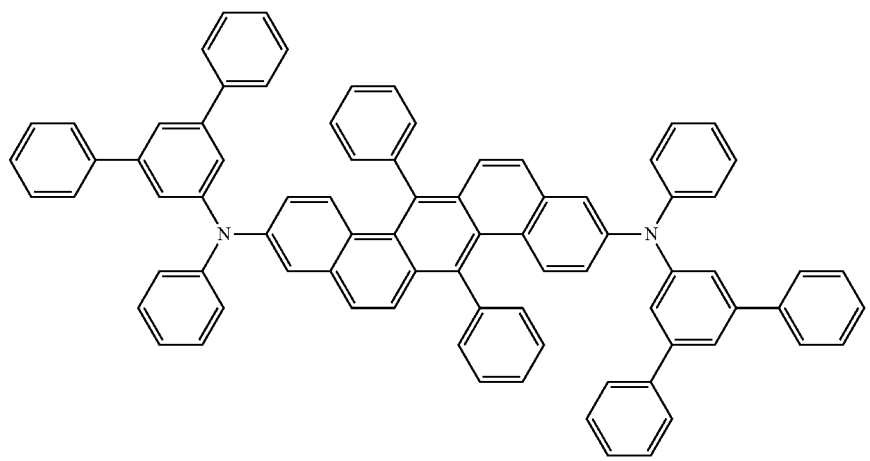 |

TABLE 1-continued
| Anthracene-containing derivative No. | Chemical structural formula of the anthracene-containing derivative |
|---|---|
| 7 | 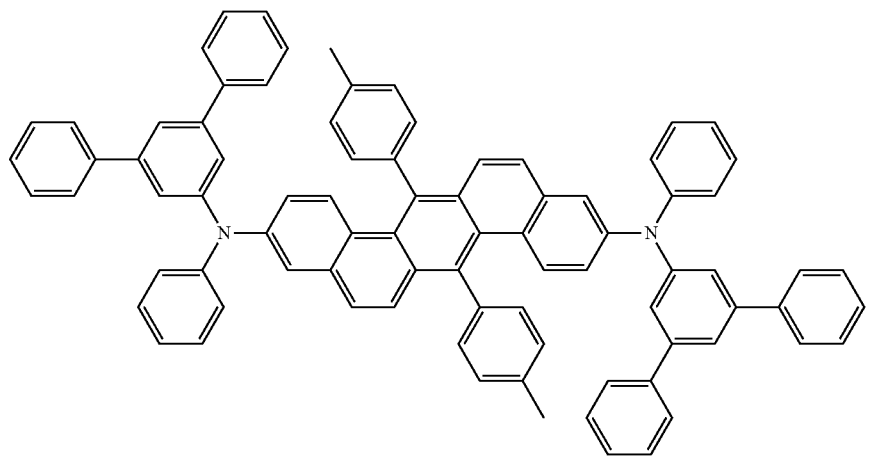 [SMILES: Cc1ccc(-c2c3ccc4cc(N(c5ccccc5)c5cc(-c6ccccc6)cc(-c6ccccc6)c5)ccc4c3c(-c3ccc(C)cc3)c3ccc4cc(N(c5ccccc5)c5cc(-c6ccccc6)cc(-c6ccccc6)c5)ccc4c23)cc1] |
| 8 | 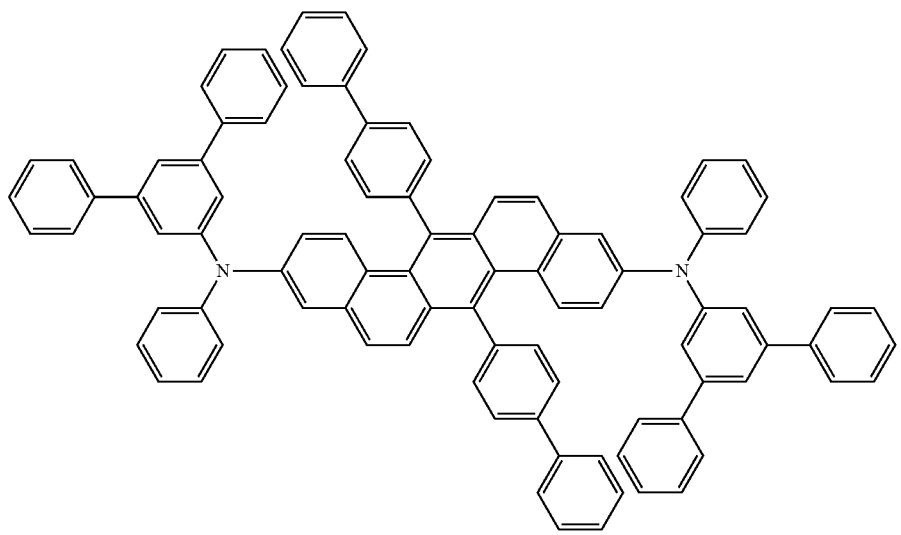 [SMILES: c1ccc(-c2ccc(-c3c4ccc5cc(N(c6ccccc6)c6cc(-c7ccccc7)cc(-c7ccccc7)c6)ccc5c4c(-c4ccc(-c5ccccc5)cc4)c4ccc5cc(N(c6ccccc6)c6cc(-c7ccccc7)cc(-c7ccccc7)c6)ccc5c34)cc2)cc1] |
| 9 | 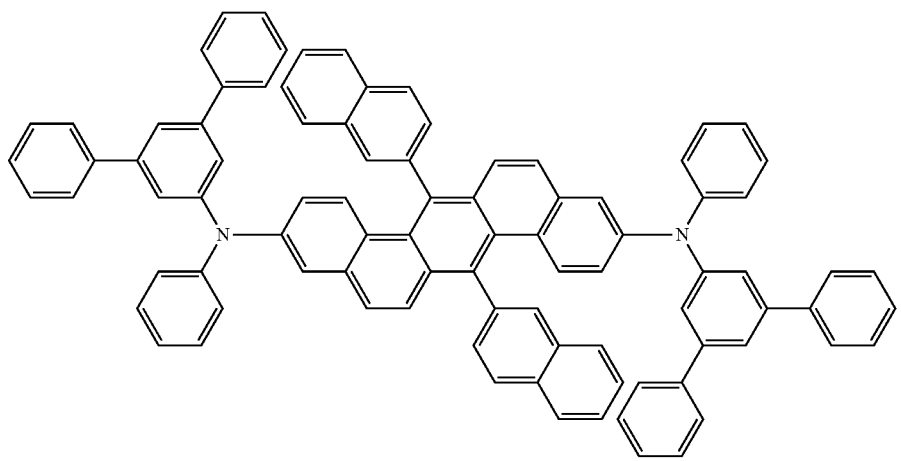 [SMILES: c1ccc(-c2cc(-c3ccccc3)cc(N(c3ccccc3)c3ccc4c(ccc5c(-c6ccc7ccccc7c6)c6c(ccc7cc(N(c8ccccc8)c8cc(-c9ccccc9)cc(-c9ccccc9)c8)ccc76)c(-c6ccc7ccccc7c6)c54)c3)c2)cc1] |

TABLE 1-continued

| Anthracene-containing derivative No. | Chemical structural formula of the anthracene-containing derivative |
|---|---|
| 10 | |
| 11 | |
| 12 | |

TABLE 1-continued
| Anthracene-containing derivative No. | Chemical structural formula of the anthracene-containing derivative |
|---|---|
| 13 | 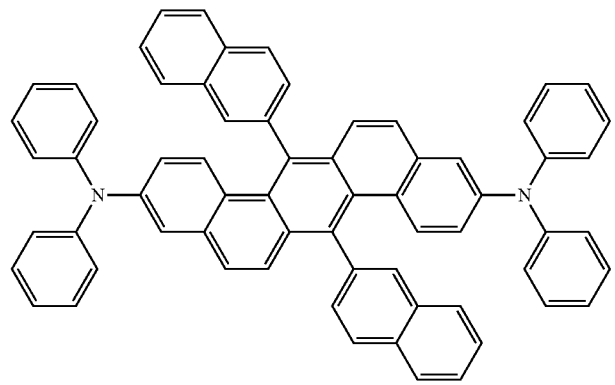 [SMILES: c1ccc(N(c2ccccc2)c2ccc3c(ccc4c(-c5ccc6ccccc6c5)c5c(ccc6cc(N(c7ccccc7)c7ccccc7)ccc65)c(-c5ccc6ccccc6c5)c43)c2)cc1] |
| 14 | 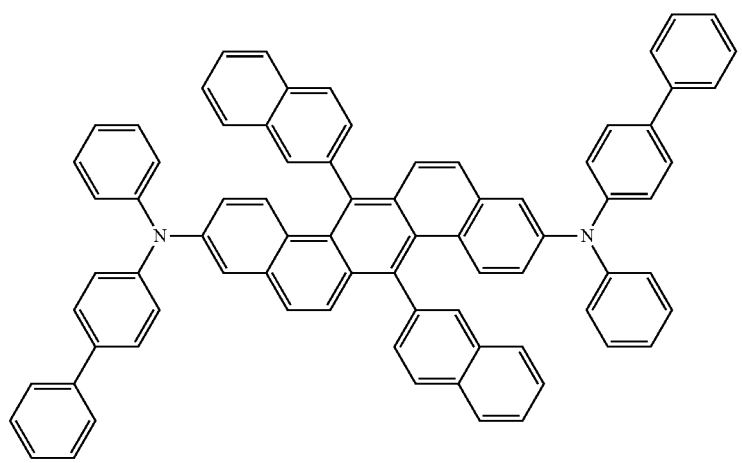 [SMILES: c1ccc(-c2ccc(N(c3ccccc3)c3ccc4c(ccc5c(-c6ccc7ccccc7c6)c6c(ccc7cc(N(c8ccccc8)c8ccc(-c9ccccc9)cc8)ccc76)c(-c6ccc7ccccc7c6)c54)c3)cc2)cc1] |
| 15 | 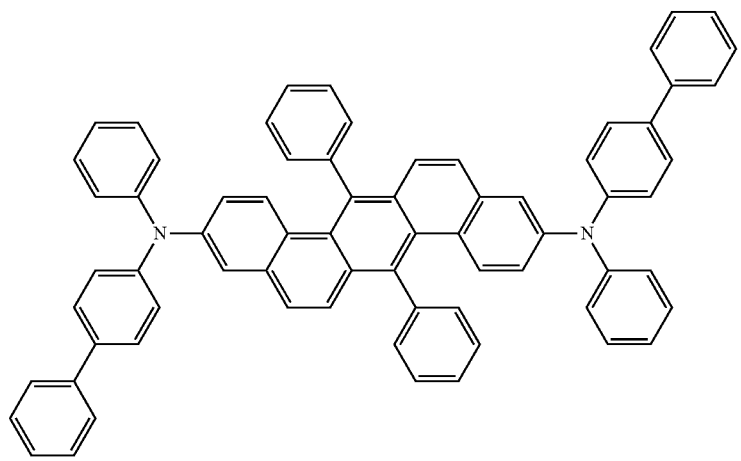 [SMILES: c1ccc(-c2ccc(N(c3ccccc3)c3ccc4c(ccc5c(-c6ccccc6)c6c(ccc7cc(N(c8ccccc8)c8ccc(-c9ccccc9)cc8)ccc76)c(-c6ccccc6)c54)c3)cc2)cc1] |

TABLE 1-continued
| Anthracene-containing derivative No. | Chemical structural formula of the anthracene-containing derivative |
|---|---|
| 16 | 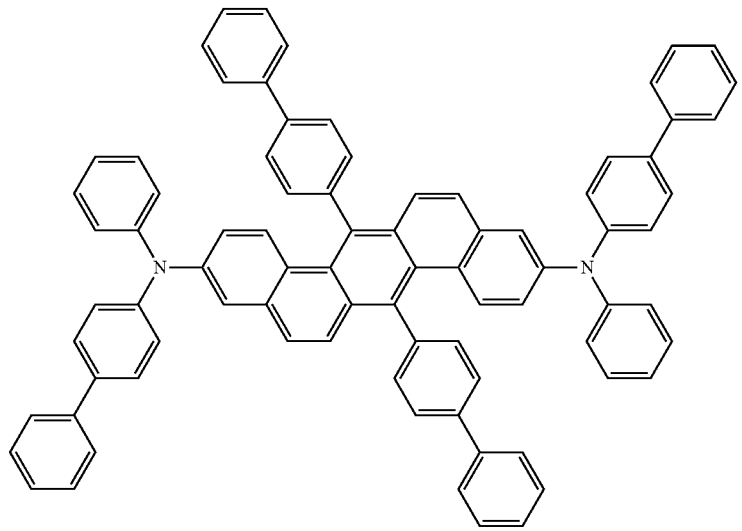 [SMILES: c1ccc(-c2ccc(-c3c4ccc5cc(N(c6ccccc6)c6ccc(-c7ccccc7)cc6)ccc5c4c(-c4ccc(-c5ccccc5)cc4)c4ccc5cc(N(c6ccccc6)c6ccc(-c7ccccc7)cc6)ccc5c34)cc2)cc1] |
| 17 | 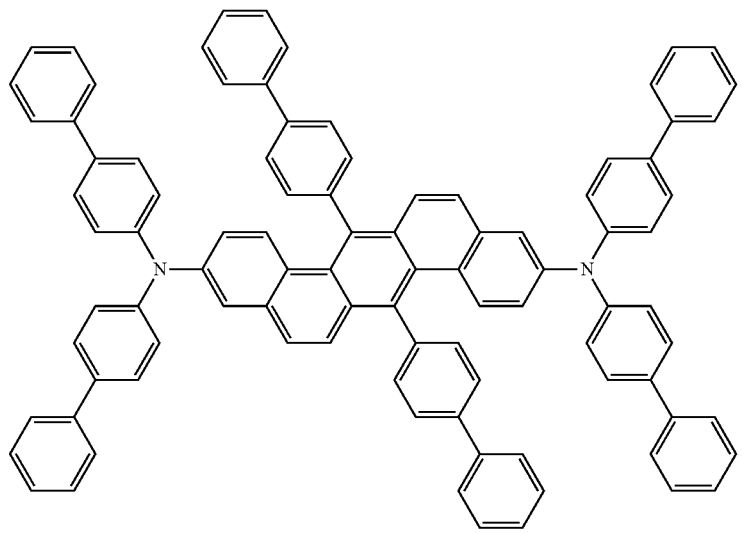 [SMILES: c1ccc(-c2ccc(-c3c4ccc5cc(N(c6ccc(-c7ccccc7)cc6)c6ccc(-c7ccccc7)cc6)ccc5c4c(-c4ccc(-c5ccccc5)cc4)c4ccc5cc(N(c6ccc(-c7ccccc7)cc6)c6ccc(-c7ccccc7)cc6)ccc5c34)cc2)cc1] |
| 18 | 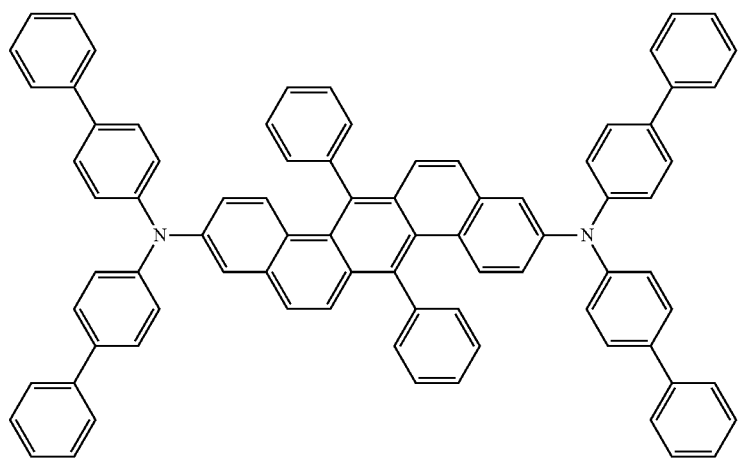 [SMILES: c1ccc(-c2ccc(N(c3ccc(-c4ccccc4)cc3)c3ccc4c(ccc5c(-c6ccccc6)c6c(ccc7cc(N(c8ccc(-c9ccccc9)cc8)c8ccc(-c9ccccc9)cc8)ccc76)c(-c6ccccc6)c54)c3)cc2)cc1] |

TABLE 1-continued
| Anthracene-containing derivative No. | Chemical structural formula of the anthracene-containing derivative |
|---|---|
| 19 | 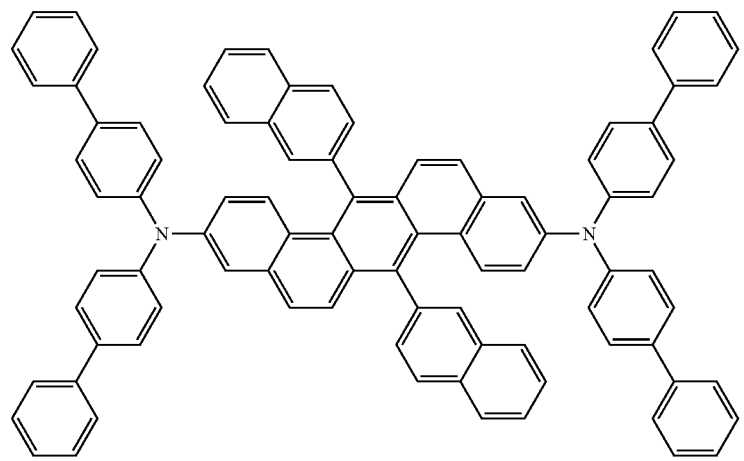 [SMILES: c1ccc(-c2ccc(N(c3ccc(-c4ccccc4)cc3)c3ccc4c(ccc5c(-c6ccc7ccccc7c6)c6c(ccc7cc(N(c8ccc(-c9ccccc9)cc8)c8ccc(-c9ccccc9)cc8)ccc76)c(-c6ccc7ccccc7c6)c54)c3)cc2)cc1] |
| 20 | 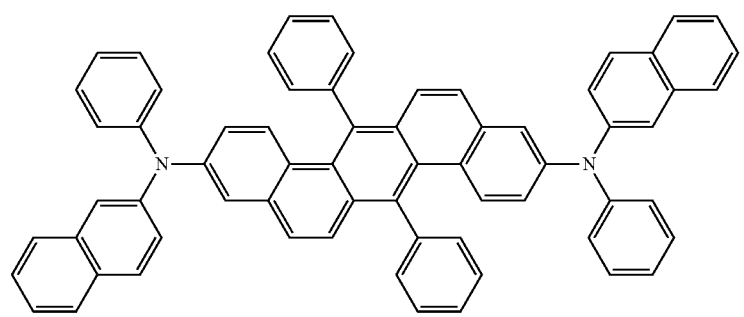 [SMILES: c1ccc(-c2c3ccc4cc(N(c5ccccc5)c5ccc6ccccc6c5)ccc4c3c(-c3ccccc3)c3ccc4cc(N(c5ccccc5)c5ccc6ccccc6c5)ccc4c23)cc1] |
| 21 | 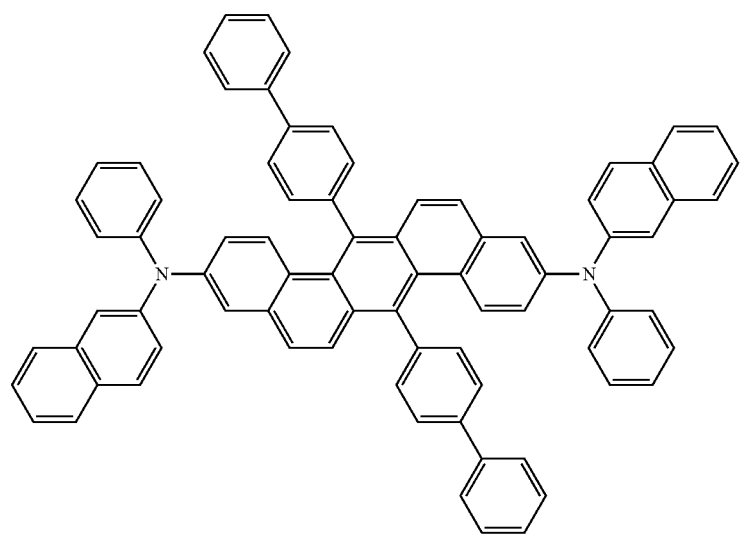 [SMILES: c1ccc(-c2ccc(-c3c4ccc5cc(N(c6ccccc6)c6ccc7ccccc7c6)ccc5c4c(-c4ccc(-c5ccccc5)cc4)c4ccc5cc(N(c6ccccc6)c6ccc7ccccc7c6)ccc5c34)cc2)cc1] |

TABLE 1-continued
| Anthracene-containing derivative No. | Chemical structural formula of the anthracene-containing derivative |
|---|---|
| 22 | 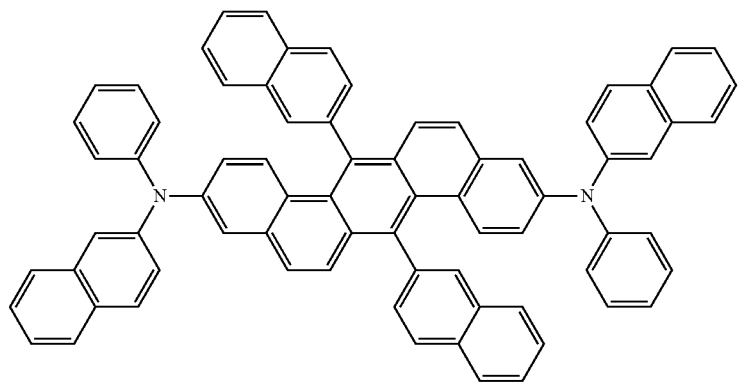 [SMILES: c1ccc(N(c2ccc3ccccc3c2)c2ccc3c(ccc4c(-c5ccc6ccccc6c5)c5c(ccc6cc(N(c7ccccc7)c7ccc8ccccc8c7)ccc65)c(-c5ccc6ccccc6c5)c43)c2)cc1] |
| 23 | 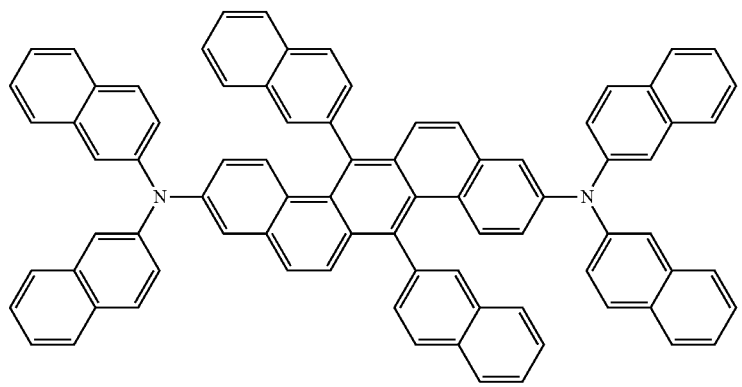 [SMILES: c1ccc2cc(-c3c4ccc5cc(N(c6ccc7ccccc7c6)c6ccc7ccccc7c6)ccc5c4c(-c4ccc5ccccc5c4)c4ccc5cc(N(c6ccc7ccccc7c6)c6ccc7ccccc7c6)ccc5c34)ccc2c1] |
| 24 | 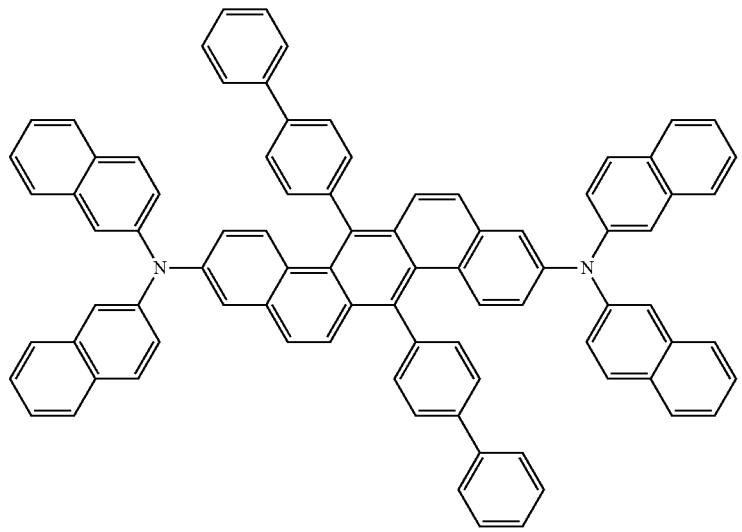 [SMILES: c1ccc(-c2ccc(-c3c4ccc5cc(N(c6ccc7ccccc7c6)c6ccc7ccccc7c6)ccc5c4c(-c4ccc(-c5ccccc5)cc4)c4ccc5cc(N(c6ccc7ccccc7c6)c6ccc7ccccc7c6)ccc5c34)cc2)cc1] |

TABLE 1-continued
| Anthracene-containing derivative No. | Chemical structural formula of the anthracene-containing derivative |
|---|---|
| 25 | 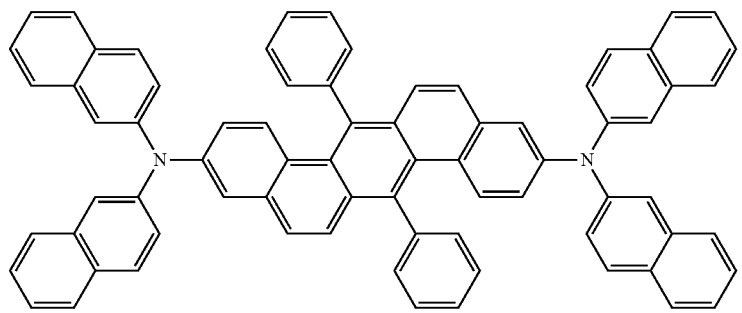 [SMILES: c1ccc(-c2c3ccc4cc(N(c5ccc6ccccc6c5)c5ccc6ccccc6c5)ccc4c3c(-c3ccccc3)c3ccc4cc(N(c5ccc6ccccc6c5)c5ccc6ccccc6c5)ccc4c23)cc1] |
| 26 | 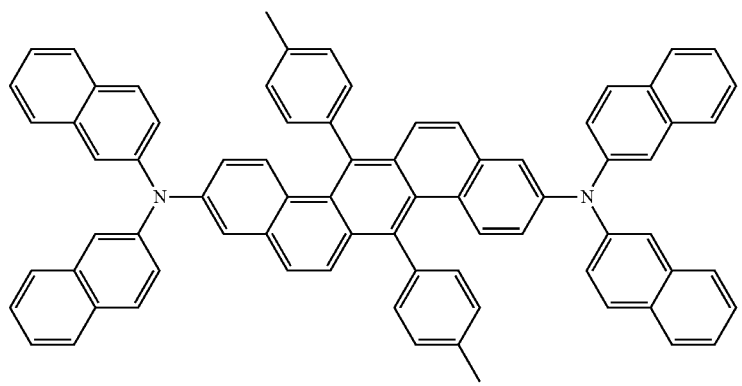 [SMILES: Cc1ccc(-c2c3ccc4cc(N(c5ccc6ccccc6c5)c5ccc6ccccc6c5)ccc4c3c(-c3ccc(C)cc3)c3ccc4cc(N(c5ccc6ccccc6c5)c5ccc6ccccc6c5)ccc4c23)cc1] |
| 27 | 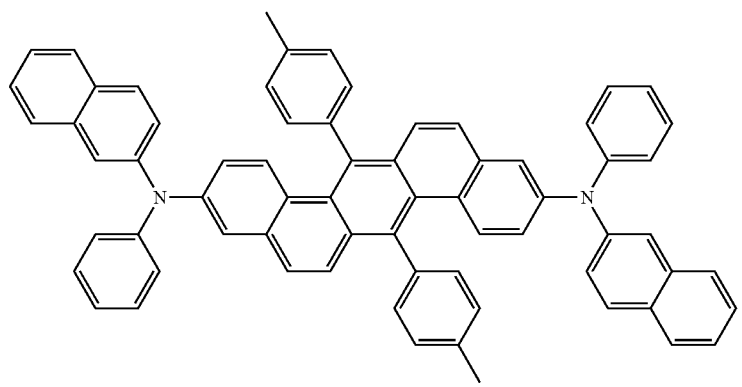 [SMILES: Cc1ccc(-c2c3ccc4cc(N(c5ccccc5)c5ccc6ccccc6c5)ccc4c3c(-c3ccc(C)cc3)c3ccc4cc(N(c5ccccc5)c5ccc6ccccc6c5)ccc4c23)cc1] |
| 28 | 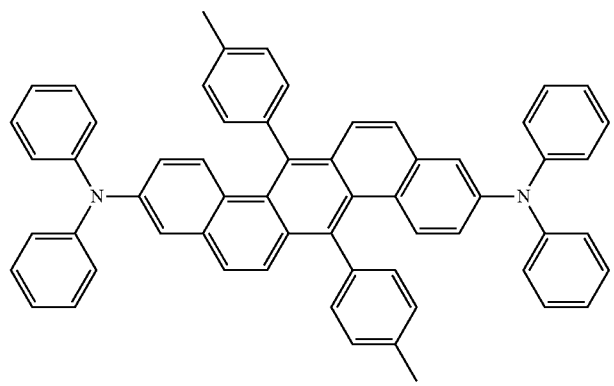 [SMILES: Cc1ccc(-c2c3ccc4cc(N(c5ccccc5)c5ccccc5)ccc4c3c(-c3ccc(C)cc3)c3ccc4cc(N(c5ccccc5)c5ccccc5)ccc4c23)cc1] |

TABLE 1-continued

| Anthracene-containing derivative No. | Chemical structural formula of the anthracene-containing derivative |
|---|---|
| 29 | 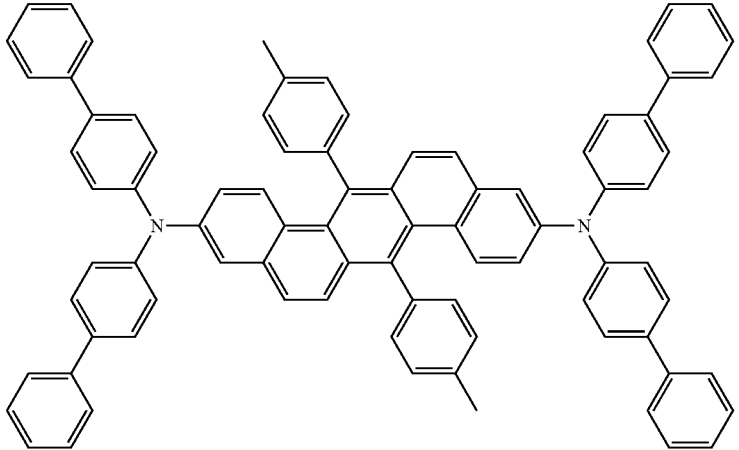 [SMILES: Cc1ccc(-c2c3ccc4cc(N(c5ccc(-c6ccccc6)cc5)c5ccc(-c6ccccc6)cc5)ccc4c3c(-c3ccc(C)cc3)c3ccc4cc(N(c5ccc(-c6ccccc6)cc5)c5ccc(-c6ccccc6)cc5)ccc4c23)cc1] |
| 30 | 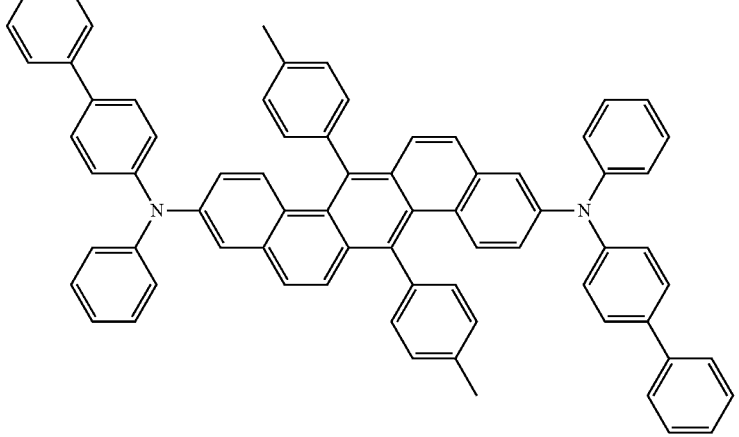 |

Based on the same inventive conception, the examples of the invention also provide a production process suitable for any one of the above described anthracene-containing derivative, as shown by FIG. 1, which specifically comprises the following steps of:

S101, under a protection gas atmosphere, adding a dibenzoanthracene bromide containing a $R_1$ group, an amine compound, sodium tert-butoxide, palladium acetate and a first organic solvent into a first reaction vessel, and continuously stirring the solution in the first reaction vessel; wherein $R_1$ group is selected from an aromatic group or a fused aromatic group having a carbon atom number of 6 to 18.

Specifically, in the specific practice, the protection gas atmosphere may be a nitrogen gas protection atmosphere, which may also be an inert gas protection atmosphere, which is not limited herein.

Specifically, in the specific practice, the first organic solvent may is toluene, which may also be other organic solvents capable of achieving the solution of the invention, which is not limited herein.

S102, adding tri-tert-butyl phosphine into the first reaction vessel dropwise, and after heating to reflux for a first predetermined time, cooling to room temperature.

Specifically, in the specific practice, slowly adding the tri-tert-butyl phosphine into the first reaction vessel dropwise produces a better effect.

Specifically, in the specific practice, the main purpose of heating to reflux is for accelerating the reaction speed. Preferably, during the heating to reflux, mixing the reactants in the first reaction vessel produces a better effect.

Specifically, in the specific practice, the setting of the first predetermined time should ensure the sufficient reaction of the reactants.

S103, upon extracting, washing, and drying, obtaining an anthracene-containing derivative.

Specifically, the main purpose of extracting and washing is for removing other impurities in the reaction solution after sufficient reaction except for the anthracene-containing derivative, so as to obtain the anthracene-containing derivative with a higher purity.

Figure 2:
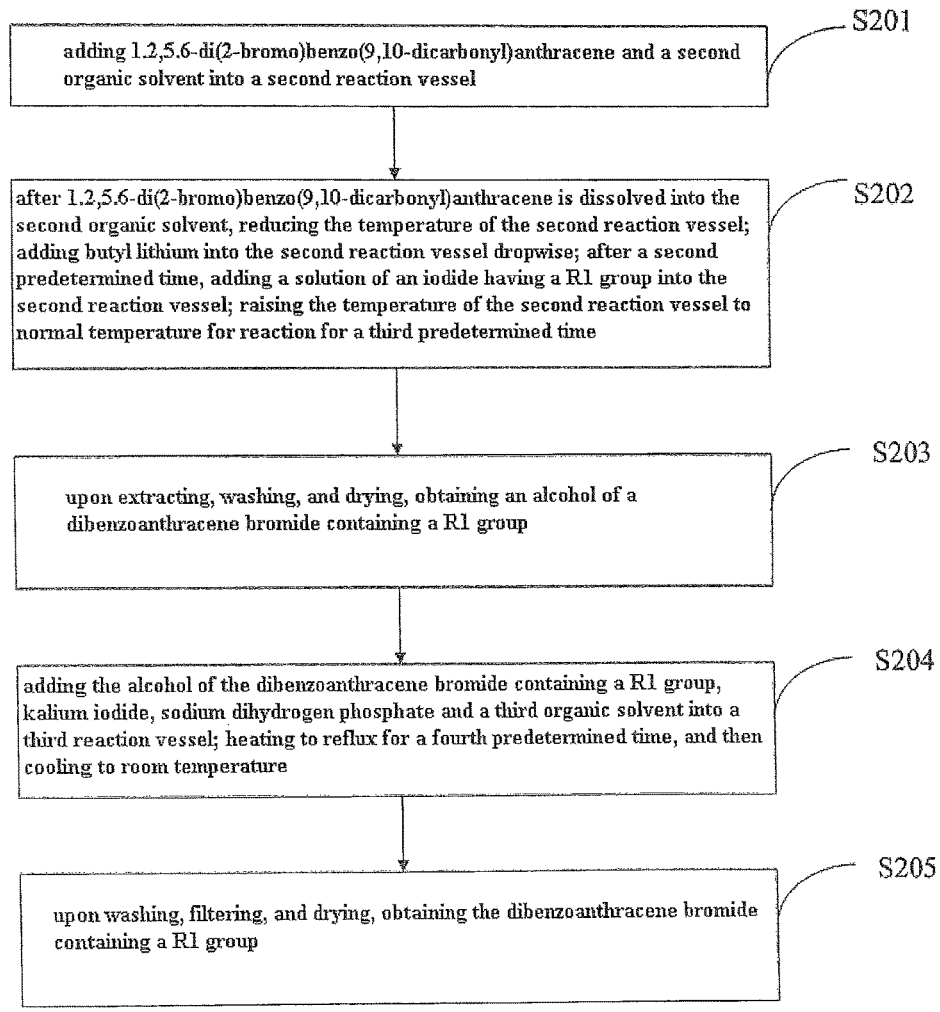
FIG. 2 is a flow chart of the production process of an dibenzoanthracene bromide containing a $R_1$ group provided by examples of the invention.

Furthermore, in the above production process provided by the examples of the invention, as shown by FIG. 2, the dibenzoanthracene bromide containing a $R_1$ group may be specifically produced from the following steps of:

S201, adding 1.2,5.6-di(2-bromo)benzo(9,10-dicarbonyl) anthracene and a second organic solvent into a second reaction vessel.

Specifically, in the specific practice, the second organic solvent may be tetrahydrofuran, and may also be other organic solvents which are capable of achieving the solution of the invention, which is not limited herein.

S202, after 1.2,5.6-di(2-bromo)benzo(9,10-dicarbonyl) anthracene is dissolved into the second organic solvent, reducing the temperature of the second reaction vessel; adding butyl lithium into the second reaction vessel dropwise; after a second predetermined time, adding a solution of an iodide having a $R_1$ group into the second reaction vessel; raising the temperature of the second reaction vessel to normal temperature for reaction for a third predetermined time;

Specifically, in the specific practice, upon the 1.2,5.6-di (2-bromo)benzo(9,10-dicarbonyl)anthracene is dissolved into the second organic solvent, reducing the temperature of the second reaction vessel to around −72 degree centigrade is preferred.

Specifically, in the specific practice, the setting principles of the second predetermined time and the third predetermined time are the same as the setting principle of the above described first predetermined time, which is not repeated herein.

S203, upon extracting, washing, and drying, obtaining an alcohol of a dibenzoanthracene bromide containing a $R_1$ group.

Specifically, the main purpose of extracting and washing is for removing the other impurities in the reaction solution after sufficient reaction except for the alcohol of dibenzoanthracene bromide containing a $R_1$ group, so as to obtain the alcohol of dibenzoanthracene bromide containing a $R_1$ group with a higher purity.

S204, adding the alcohol of the dibenzoanthracene bromide containing a $R_1$ group, potassium iodide, sodium dihydrogen phosphate and a third organic solvent into a third reaction vessel; heating to reflux for a fourth predetermined time, and then cooling to room temperature.

Specifically, in the specific practice, the third organic solvent is glacial acetic acid, and it may also be other organic solvents which are capable of achieving the solution of the invention, which is not limited herein.

Specifically, in the specific practice, the setting principle of the fourth predetermined time is the same as the setting principle of the above described first predetermined time, which is not repeated herein.

S205, upon washing, filtering, and drying, obtaining the dibenzoanthracene bromide containing a $R_1$ group.

Specifically, the main purpose of washing and filtering is for removing other impurities in the reaction solution after sufficient reaction except for dibenzoanthracene bromide containing a $R_1$ group, so as to obtain the dibenzoanthracene bromide containing a $R_1$ group with a higher purity.

Figure 3:
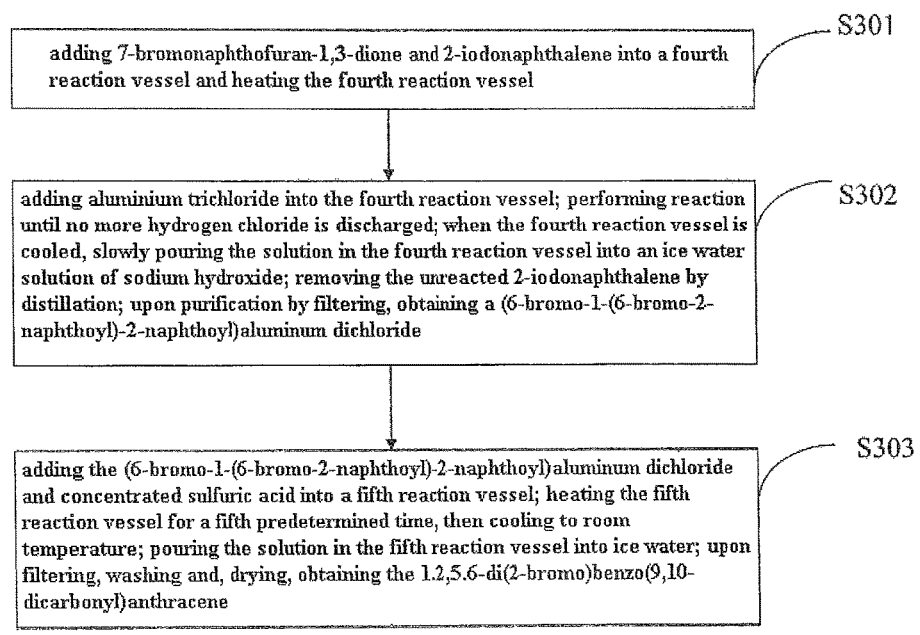
FIG. 3 is a flow chart of the production process of 1.2,5.6-di(2-bromo)benzo(9,10-dicarbonyl)anthracene provided by examples of the invention.

Furthermore, in the above production process provided by the examples of the invention, as shown by FIG. 3, 1.2,5.6-di(2-bromo)benzo(9,10-dicarbonyl)anthracene may specifically produced by the following steps of:

S301, adding 7-bromonaphthofuran-1,3-dione and 2-iodonaphthalene into a fourth reaction vessel and heating the fourth reaction vessel.

Specifically, in the specific practice, upon adding 7-bromonaphthofuran-1,3-dione and 2-iodonaphthalene into the fourth reaction vessel, heating the fourth reaction vessel to between 110° C. and 120° C. is preferred.

S302, adding aluminium trichloride into the fourth reaction vessel; performing reaction until no more hydrogen chloride is discharged; when the fourth reaction vessel is cooled, slowly pouring the solution in the fourth reaction vessel into an ice water solution of sodium hydroxide; removing the unreacted 2-iodonaphthalene by distillation; upon purification by filtering, obtaining a (6-bromo-1-(6-bromo-2-naphthoyl)-2-naphthoyl)aluminum dichloride.

Specifically, in the specific practice, upon cooling the temperature of the fourth reaction vessel to around 90° C., slowly pouring the solution in the fourth reaction vessel into an ice water solution of sodium hydroxide is preferred.

S303, adding the (6-bromo-1-(6-bromo-2-naphthoyl)-2-naphthoyl)aluminum dichloride and concentrated sulfuric acid into a fifth reaction vessel; heating the fifth reaction vessel for a fifth predetermined time, then cooling to room temperature; pouring the solution in the fifth reaction vessel into ice water; upon filtering, washing and, drying, obtaining the 1.2,5.6-di(2-bromo)benzo(9,10-dicarbonyl)anthracene.

Specifically, in the specific practice, selecting a concentrated sulfuric acid with a concentration of 96% as the concentrated sulfuric acid is preferred.

Specifically, in the specific practice, the setting principle of the fifth predetermined time is the same as the setting principle of the above described first predetermined time, which is not repeated herein.

Specifically, the main purpose of filtering and washing is for removing other impurities in the reaction solution after sufficient reaction except for 1.2,5.6-di(2-bromo)benzo(9, 10-dicarbonyl)anthracene, so as to obtain 1.2,5.6-di(2-bromo)benzo(9,10-dicarbonyl)anthracene with a higher purity.

Specifically, the production of 1.2,5.6-di(2-diphenylamino)benzo(9,10-diphenyl)anthracene (No. 1 in Table 1) employing the above described process is illustrated below for specifically describing the above described production process of anthracene-containing derivative provided by examples of the invention, and the specific production process is as follows:

Firstly, 1.2,5.6-di(2-bromo)benzo(9,10-dicarbonyl)anthracene is produced specifically by the steps of:

(1) placing 119.14 g (correspond to 0.43 mol) of 7-bromonaphthofuran-1,3-dione and 162.60 g (correspond to 0.64 mol) of 2-iodonaphthalene into a 250 mL three neck flask, mixing and heating to from 110° C. to 120° C.;

(2) adding 57 g (correspond to 0.43 mol) of aluminium trichloride into the three neck flask and then reacting for about 6 hours, until no more hydrogen chloride is discharged, cooling the reaction solution to about 90° C.;

(3) slowly pouring the solution in the above described three neck flask into 120 mL of an ice water solution of sodium hydroxide with a concentration of 20%;

(4) removing the unreacted 2-iodonaphthalene by distillation; then filtering, and washing the cake with water; combining the filtrate and the washing solution obtained after washing the cake, adding a hydrochloric acid solution with a concentration of 20% into the combined filtrate and washing solution until the above mixed solution of the filtrate and washing solution to be neutral; filtering, washing the cake, and drying, obtaining (6-bromo-1-(6-bromo-2-naphthoyl)-2-naphthoyl)aluminum dichloride;

(5) placing the above described (6-bromo-1-(6-bromo-2-naphthoyl)-2-naphthoyl)aluminum dichloride and 21.5 g of concentrated sulfuric acid with a concentration of 96% into a three neck flask with a capability of 100 mL, heating the three neck flask to about 150° C., reacting for about 4 hours; cooling the three neck flask to room temperature, pouring the solution in the three neck flask into 300 mL of ice water, and mixing the ice water during the pouring;

(6) filtering, washing the case water, and combining filtrate obtained after filtering and the washing solution obtained after washing the cake, adding sodium hydroxide solution with a concentration of 5% into the combined filtrate and washing solution until the above mixed solution of the filtrate and washing solution to be neutral;

(7) drying and then recrystallizating with glacial acetic acid, obtaining 120.25 g of dark brown 1.2,5.6-di(2-bromo)benzo(9,10-dicarbonyl)anthracene, with a yield of up to 60.0%.

Specifically, the chemical reaction scheme of the above described production of 1.2,5.6-di(2-bromo)benzo(9,10-dicarbonyl)anthracene is as follows:

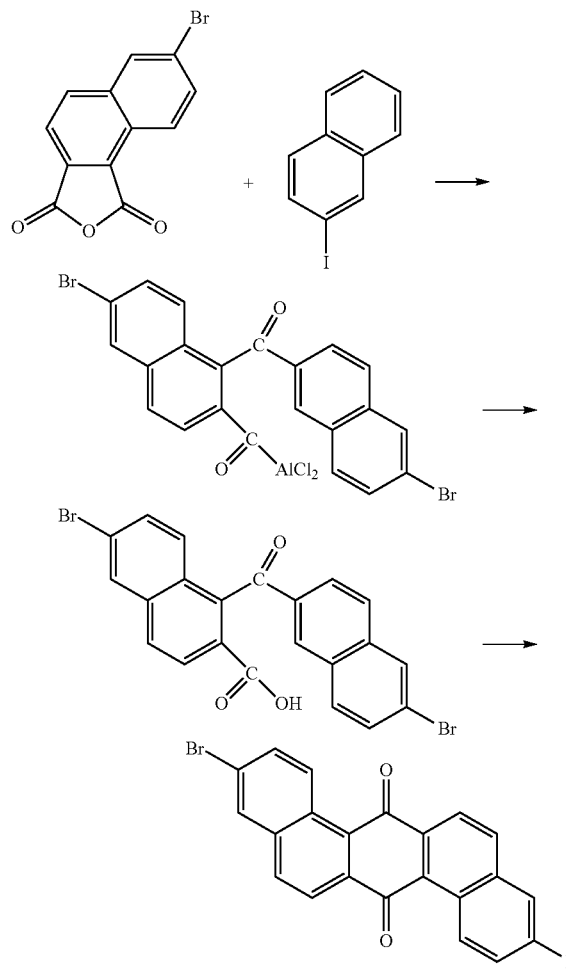

Then, a 1.2,5.6-di(2-bromo)benzo(9,10-diphenyl)anthracene compound is produced by from 1.2,5.6-di(2-bromo)benzo(9,10-dicarbonyl)anthracene and iodobenzene specifically by the steps of.

(1) adding 46.61 g (correspond to 0.1 mol) of 1.2,5.6-di(2-bromo)benzo(9,10-dicarbonyl)anthracene and a 200 mL tetrahydrofuran solution into a first reaction vessel, mixing at normal temperature for about 10 minutes;

(2) upon completely dissolving 1.2,5.6-di(2-bromo)benzo(9,10-dicarbonyl)anthracene into the tetrahydrofuran solution, reducing the temperature to −72° C., slowly adding 96 mL of butyl lithium (n-BuLi) into the first reaction vessel dropwise;

(3) after reacting at low temperature for about 3 hours, adding 100 mL of a tetrahydrofuran solution containing 37.68 g (correspond to 0.24 mmol) of iodobenzene into the first reaction vessel, and then slowly rising the temperature to normal temperature, and mixing the reactants in the reaction vessel for about 24 hours;

(4) after adding 300 mL of distilled water, 300 mL of an over saturated solution of $NH_4Cl$ and 300 mL of a dichloromethane solution into the first reaction vessel, mixing the mixed solution in the first reaction vessel for about 2 hours;

(5) extracting the organic layer, drying under reduced pressure, adding the dried solid into 500 mL of an acetone solution and mixing for about 1 hour;

filtering, concentrating the organic solvent under reduced pressure, obtaining 43.19 g of a light brown solid 1.2,5.6-di(2-bromo)benzo(9,10-diphenyl-9,10-dihydroxyl)anthracene compound, with a yield of up to 69%;

(6) adding 31.32 g (correspond to 0.05 mol) of a 1.2,5.6-di(2-bromo)benzo(9,10-diphenyl-9,10-dihydroxyl)anthracene compound, 8.3 g (correspond to 0.05 mol) of potassium iodide, 12.0 g (correspond to 0.1 mol) of sodium dihydrogen phosphate, and 200 mL of glacial acetic acid into a second reaction vessel, mixing under refluxing to react for about 20 hours; cooling the second reaction vessel to room temperature, adding 200 mL of distilled water into the second reaction vessel and mixing;

(7) filtering under reduced pressure, adding the obtained solid into 200 mL of an over saturated $NaHCO_3$ solution, mixing for 30 minutes; filtering under reduced pressure, washing the obtained solid with 200 mL of an over saturated NaCl solution; and then washing the obtained solid with 300 mL of distilled water; filtering under reduced pressure, and drying the obtained solid in vacuum at room temperature, obtaining 24.29 g of a dark yellow 1.2,5.6-di(2-bromo)benzo(9,10-diphenyl)anthracene compound, with a yield of up to 82%.

Specifically, the chemical reaction scheme of the above described production of 1.2,5.6-di(2-bromo)benzo(9,10-diphenyl)anthracene compound employing 1.2,5.6-di(2-bromo)benzo(9,10-dicarbonyl)anthracene and iodobenzene is as follows:

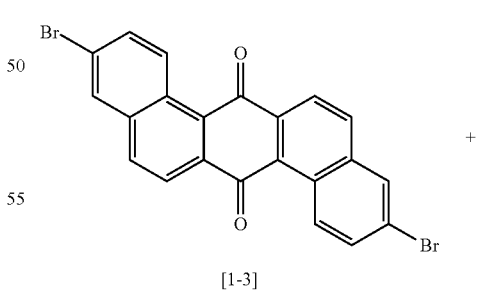

[1-3]

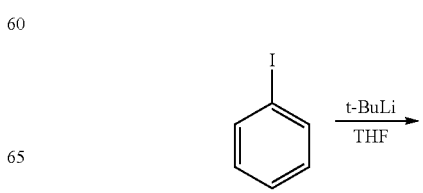

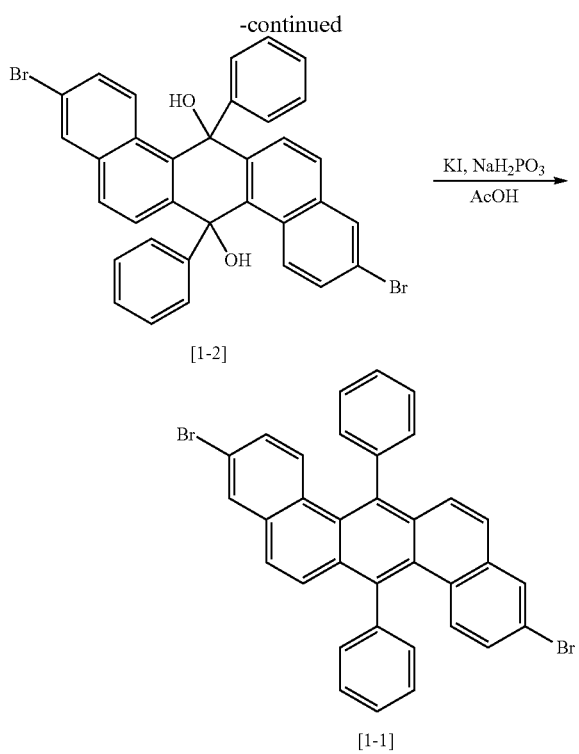

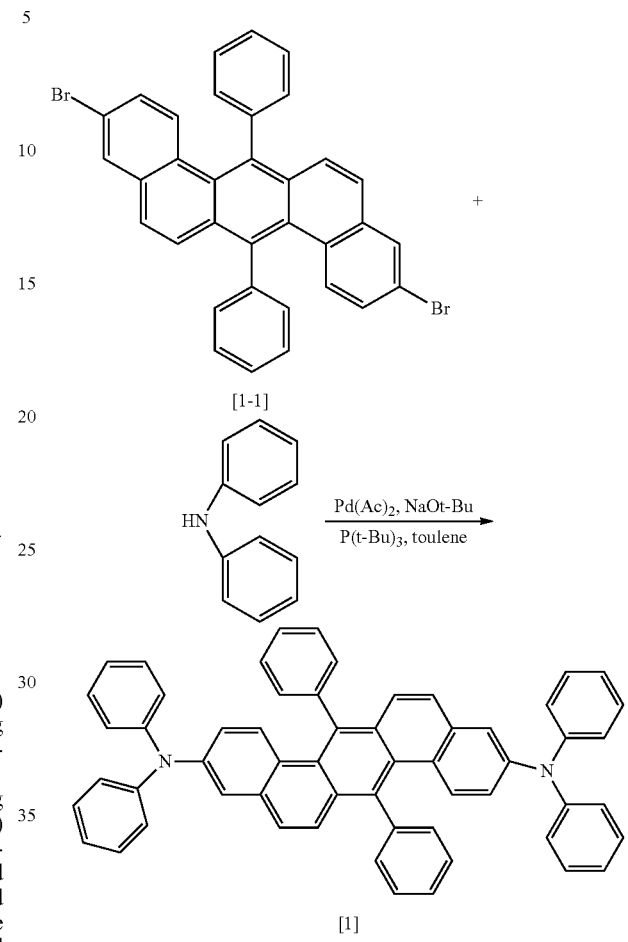

Finally, 1.2,5.6-di(2-diphenylamino)benzo(9,9-diphenyl)anthracene (No. 1 in Table 1) is produced by employing 1.2,5.6-di(2-bromo)benzo(9,10-diphenyl)anthracene compound and diphenylamine by the steps of:

(1) under a nitrogen gas protection atmosphere, adding 23.70 g (correspond to 0.04 mol) of 1.2,5.6-di(2-bromo)benzo(9,10-diphenyl)anthracene compound, 16.24 g (correspond to 0.096 mol) of diphenylamine, 10.76 g (correspond to 0.112 mol) of sodium tert-butoxide, 44.9 mg (correspond to 0.2 mmol) of palladium acetate, and 200 mL of toluene into a third reaction vessel, mixing the solution in the third reaction vessel for about 1 hour;

(2) slowly adding 40.46 mg (correspond to 0.2 mmol) of tri-tert-butyl phosphine into the third reaction vessel dropwise, refluxing and mixing the solution in the third reaction vessel for about 1 g hours, cooling the third reaction vessel to room temperature;

(3) upon adding 200 mL of distilled water and 200 mL of dichloromethane into the third reaction vessel, mixing the solution in the third reaction vessel for about 2 hours;

(4) washing the solution in the third reaction vessel with methanol and acetone;

(5) filtering under a reduced pressure, drying in vacuum at room temperature, obtaining 20.30 g of a yellow solid 1.2,5.6-di(2-diphenylamino)benzo(9,9-diphenyl)anthracene (No. 1 in Table 1), with a yield of 66%.

Specifically, the chemical reaction scheme of the above described production of the anthracene-containing derivative (No. 1 in Table 1) employing 1.2,5.6-di(2-bromo)benzo(9,10-diphenyl)anthracene compound and diphenylamine is as follows:

The above described specific production process is illustrated using the anthracene-containing derivative No. 1 in Table 1 to describe the above described production process provided by the examples of the invention. The anthracene-containing derivatives with other numbers in Table 1 may also be similarly produced by changing iodide having a $R_1$ group and the specific material of the amine compound according to the specific requirements. The produced anthracene-containing derivatives may be analyzed in the manner of a fast atom bombardment ionization method to obtain the molecular formula of each anthracene-containing derivative, and the mass percents of the carbon element, the hydrogen element, and the nitrogen element can be measured by elemental analysis. The measured results are compared with the theoretically calculated results, and specific data thereof are as shown by the following Table 2.

TABLE 2

| Anthracene-containing derivative No. | Elemental Analysis | Fast atom bombardment mass spectrum (g/mol) |
|---|---|---|
| 1 | Calculated values are C: 91.70%; H: 5.41%; N: 2.89%; Measured values are C: 91.70%; H: 5.40%; N: 2.90%; | 969.22 |

TABLE 2-continued

| Anthracene-containing derivative No. | Elemental Analysis | Fast atom bombardment mass spectrum (g/mol) |
|---|---|---|
| 2 | Calculated values are C: 92.44%; H: 5.05%; N: 2.51%; Measured values are C: 92.45%; H: 5.06%; N: 2.49%; | 1117.38 |
| 3 | Calculated values are C: 92.71%; H: 5.08%; N: 2.21%; Measured values are C: 92.72%; H: 5.07%; N: 2.21%; | 1269.57 |
| 4 | Calculated values are C: 92.45%; H: 4.92%; N: 2.63%; Measured values are C: 92.47%; H: 4.91%; N: 2.62%; | 1065.3 |
| 5 | Calculated values are C: 92.75%; H: 4.84%; N: 2.40%; Measured values are C: 92.74%; H: 4.83%; N: 2.42%; | 1165.42 |
| 6 | Calculated values are C: 91.93%; H: 5.46%; N: 2.61%; Measured values are C: 91.93%; H: 5.44%; N: 2.63%; | 1071.35 |
| 7 | Calculated values are C: 91.77%; H: 5.68%; N: 2.55%; Measured values are C: 91.76%; H: 5.69%; N: 2.55%; | 1099.4 |
| 8 | Calculated values are C: 91.97%; H: 5.75%; N: 2.28%; Measured values are C: 91.96%; H: 5.75%; N: 2.29%; | 1227.58 |
| 9 | Calculated values are C: 92.43%; H: 5.17%; N: 2.40%; Measured values are C: 92.42%; H: 5.16%; N: 2.42%; | 1169.45 |
| 10 | Calculated values are C: 92.71%; H: 5.08%; N: 2.21%; Measured values are C: 92.70%; H: 5.10%; N: 2.20%; | 1269.57 |
| 11 | Calculated values are C: 91.07%; H: 5.27%; N: 3.66%; Measured values are C: 91.08%; H: 5.28%; N: 2.64%; | 764.95 |
| 12 | Calculated values are C: 91.67%; H: 5.28%; N: 3.05%; Measured values are C: 91.66%; H: 5.30%; N: 3.04%; | 917.14 |
| 13 | Calculated values are C: 91.64%; H: 5.13%; N: 3.24%; Measured values are C: 91.66%; H: 5.12%; N: 3.23%; | 865.07 |
| 14 | Calculated values are C: 92.09%; H: 5.15%; N: 2.75%; Measured values are C: 92.09%; H: 5.17%; N: 2.73%; | 1017.26 |
| 15 | Calculated values are C: 91.47%; H: 5.48%; N: 3.05%; Measured values are C: 91.46%; H: 5.48%; N: 3.06%; | 919.16 |
| 16 | Calculated values are C: 91.93%; H: 5.46%; N: 2.61%; Measured values are C: 91.70%; H: 5.41%; N: 2.89%; | 1071.35 |
| 17 | Calculated values are C: 92.27%; H: 5.44%; N: 2.29%; Measured values are C: 91.70%; H: 5.41%; N: 2.89%; | 1223.54 |
| 18 | Calculated values are C: 91.93%; H: 5.46%; N: 2.61%; Measured values are C: 91.70%; H: 5.41%; N: 2.89%; | 1071.35 |
| 19 | Calculated values are C: 92.43%; H: 5.17%; N: 2.40%; Measured values are C: 91.70%; H: 5.41%; N: 2.89%; | 1169.45 |
| 20 | Calculated values are C: 91.42%; H: 5.35%; N: 3.23%; Measured values are C: 91.70%; H: 5.41%; N: 2.89%; | 867.08 |
| 21 | Calculated values are C: 91.91%; H: 5.34%; N: 2.75%; Measured values are C: 91.70%; H: 5.41%; N: 2.89%; | 1019.28 |
| 22 | Calculated values are C: 92.08%; H: 5.01%; N: 2.90%; Measured values are C: 91.70%; H: 5.41%; N: 2.89%; | 965.19 |
| 23 | Calculated values are C: 92.45%; H: 4.92%; N: 2.63%; Measured values are C: 91.70%; H: 5.41%; N: 2.89%; | 1065.3 |
| 24 | Calculated values are C: 92.44%; H: 5.05%; N: 2.51%; Measured values are C: 91.70%; H: 5.41%; N: 2.89%; | 1117.38 |
| 25 | Calculated values are C: 91.89%; H: 5.21%; N: 2.90%; Measured values are C: 91.70%; H: 5.41%; N: 2.89%; | 967.2 |
| 26 | Calculated values are C: 91.90%; H: 5.28%; N: 2.82%; Measured values are C: 91.70%; H: 5.41%; N: 2.89%; | 993.24 |
| 27 | Calculated values are C: 91.24%; H: 5.63%; N: 3.13%; Measured values are C: 91.70%; H: 5.41%; N: 2.89%; | 895.14 |
| 28 | Calculated values are C: 90.42%; H: 6.07%; N: 3.51%; Measured values are C: 91.70%; H: 5.41%; N: 2.89%; | 797.04 |
| 29 | Calculated values are C: 91.77%; H: 5.68%; N: 2.55%; Measured values are C: 91.70%; H: 5.41%; N: 2.89%; | 1099.4 |
| 30 | Calculated values are C: 91.30%; H: 5.75%; N: 2.96%; Measured values are C: 91.70%; H: 5.41%; N: 2.89%; | 947.21 |

From the data of Table 2 it can be known that, in each anthracene-containing derivative, the difference between the measurement results and the theoretical calculated results of the mass presents of carbon element, hydrogen element, and nitrogen element are very small, therefore it may be determined that, the compounds provided by the above described production process provided by examples of the invention are the anthracene-containing derivative Nos. 1 to 30 in Table 1.

Based on the same inventive conception, the examples of the invention also provide an organic electroluminescent display device, comprising: a base substrate, an organic electroluminescent element provided on the base substrate; wherein the organic electroluminescent element comprises: an anode and a cathode provided opposite to each other, and an organic light emitting material provided between the anode and the cathode;

at least one of the green phosphorescent host material, the green fluorescent host material, the hole injection material, or the hole transporting material in the organic light emitting material is any one of the anthracene-containing derivative provided by the above described examples.

Examples of the invention provide the above described organic electroluminescent display device. Because at least one of the green phosphorescent host material, the green fluorescent host material, the hole injection material, or the hole transporting material in the organic light emitting material is the anthracene-containing derivative, from the test results it can be known that, the light emitting efficiency and the light emitting brightness of this organic electroluminescent display device are both improved.

Specifically, in the OLED display device, the organic light emitting material between the anode and the cathode generally means, the hole injection layer, the hole transporting layer, the light emitting layer, the electron transporting layer, and the electron injection layer provided between the anode and the cathode, wherein the light emitting layer is generally composed of a host material and a doping material.

Specifically, in order to test the light emitting efficiency and the light emitting strength of the organic electroluminescent display devices provided by examples of the invention, each of the anthracene-containing derivatives Nos. 1-30 in Table 1 are used for producing an organic electroluminescent element testing sample, and numbering each testing sample according to the number of the anthracene-containing derivative in Table 1 contained in the testing sample.

Specifically, the organic electroluminescent element of each testing sample comprises: an anode made of a material of ITO; a 80 nm hole injection layer made of a material of 2-TNATA; a 30 nm hole transporting layer made of a material of α-NPD (N,N'-dinaphthyl-N,N'-diphenyl diphenylamine); a 30 nm light emitting layer, wherein the host light emitting material is one anthracene-containing derivative in Table 1, the doping material is compound b with a doping rate of 3%; a 30 nm cathode transmission layer made of a material of $Alq_3$; a 0.5 nm cathode injection layer made of a material of LiF; a 60 nm cathode made of a material of Al.

In order to compare the light emitting efficiency and the light emitting strength of each testing sample, the reference sample employs the compound a for replacing the anthracene-containing derivative used as the host light emitting material in testing samples, wherein the compounds a and b are all organic light emitting materials in the prior art. The compound a has a chemical structural formula of:

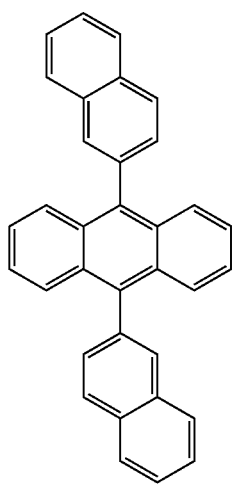 [SMILES: c1ccc2cc(-c3c4ccccc4c(-c4ccc5ccccc5c4)c4ccccc34)ccc2c1]

and the compound b has a chemical structural formula of:

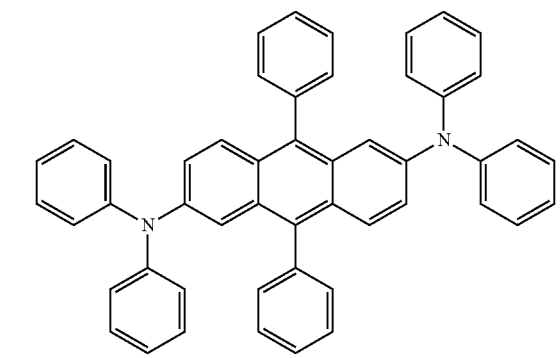 [SMILES: c1ccc(-c2c3ccc(N(c4ccccc4)c4ccccc4)cc3c(-c3ccccc3)c3ccc(N(c4ccccc4)c4ccccc4)cc23)cc1]

A reference sample and the testing samples provided by examples of the invention may be subjected to the tests for light emitting brightness and light emitting efficiency, respectively. The test results are as shown by the following Table 3.

TABLE 3

| Sample No. | Host light emitting material | Doping light emitting material | Light emitting brightness [cd/m$^2$] | Light emitting Efficiency [cd/A] |
| --- | --- | --- | --- | --- |
| Reference Sample 1 | a | b | 2032 | 20.3 |
| Testing Sample 1 | 1 | b | 2366 | 23.7 |
| Testing Sample 2 | 2 | b | 2329 | 23.3 |
| Testing Sample 3 | 3 | b | 2341 | 23.4 |
| Testing Sample 4 | 4 | b | 2433 | 24.3 |
| Testing Sample 5 | 5 | b | 2433 | 24.3 |
| Testing Sample 6 | 6 | b | 2220 | 22.2 |
| Testing Sample 7 | 7 | b | 2111 | 21.1 |
| Testing Sample 8 | 8 | b | 2069 | 20.7 |
| Testing Sample 9 | 9 | b | 2328 | 23.3 |
| Testing Sample 10 | 10 | b | 2299 | 23.0 |
| Testing Sample 11 | 11 | b | 2431 | 24.3 |
| Testing Sample 12 | 12 | b | 2238 | 22.3 |
| Testing Sample 13 | 13 | b | 2247 | 22.5 |
| Testing Sample 14 | 14 | b | 2230 | 22.3 |
| Testing Sample 15 | 15 | b | 2091 | 20.9 |
| Testing Sample 16 | 16 | b | 2158 | 21.6 |
| Testing Sample 17 | 17 | b | 2237 | 22.4 |
| Testing Sample 18 | 18 | b | 2422 | 24.2 |
| Testing Sample 19 | 19 | b | 2121 | 21.2 |
| Testing Sample 20 | 20 | b | 2242 | 22.4 |
| Testing Sample 21 | 21 | b | 2302 | 23.0 |
| Testing Sample 22 | 22 | b | 2049 | 20.5 |
| Testing Sample 23 | 23 | b | 2433 | 24.3 |
| Testing Sample 24 | 24 | b | 2215 | 22.2 |
| Testing Sample 25 | 25 | b | 2116 | 21.2 |
| Testing Sample 26 | 26 | b | 2072 | 20.7 |
| Testing Sample 27 | 27 | b | 2327 | 23.3 |
| Testing Sample 28 | 28 | b | 2289 | 22.9 |
| Testing Sample 29 | 29 | b | 2435 | 24.4 |
| Testing Sample 30 | 30 | b | 2230 | 22.3 |

From test results of Table 3 it can be known that, the light emitting brightness and the light emitting efficiency of Testing Samples provided by examples of the invention are significantly higher than those in the reference sample, such that it can be known that the above described anthracene-containing derivative provided by examples of the invention may be applied to the organic light emitting material in the organic electroluminescent display device, which may improve the light emitting efficiency and the light emitting brightness of the organic electroluminescent display device.

Examples of the invention provide an anthracene-containing derivative, a production process thereof, and an organic electroluminescent display device, and this anthracene-containing derivative is used as a green phosphorescent host material, a green fluorescent host material, a hole injection material or a hole transporting material in an organic electroluminescent display device, wherein the anthracene-containing derivative has a general molecular structural formula of:

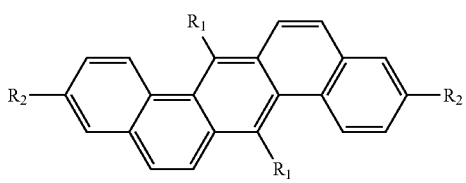

wherein $R_1$ group is selected from an aromatic group or a fused aromatic group having a carbon atom number of 6 to 18, and $R_2$ group is selected from an amine group. Examples of the invention provide above described anthracene-containing derivatives. From the test results it can be known that, by employing the above described anthracene-containing derivative as the green phosphorescent host material, the green fluorescent host material, the hole injection material, or the hole transporting material in the organic electroluminescent display device, the light emitting efficiency and the light emitting brightness of the organic electroluminescent display device may be improved.

Obviously, a person skilled in the art may conduct various modifications and alternatives to the invention without departing from the sprit and the scope of the invention. In this way, provided that these modifications and alternatives of the invention belong to the scope of claims of the invention and the equivalent techniques thereof, the invention also intends to comprise these modifications and alternatives.

What is claimed is:

1. A production process of an anthracene-containing derivative, which is used as a green phosphorescent host material, a green fluorescent host material, a hole injection material or a hole transporting material in an organic electroluminescent display device, wherein the anthracene-containing derivative has a general molecular structural formula of:

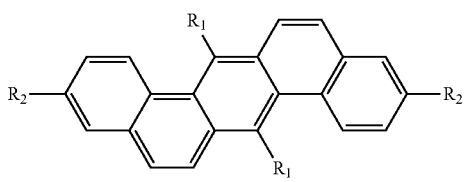

wherein $R_1$ group is selected from an aromatic group or a fused aromatic group having a carbon atom number of 6 to 18, and $R_2$ group is selected from an amine group, comprising the steps of:
under a protection gas atmosphere, adding a dibenzoanthracene bromide containing a $R_1$ group, an amine compound, sodium tert-butoxide, palladium acetate and a first organic solvent into a first reaction vessel, and continuously stirring the solution in the first reaction vessel;

wherein $R_1$ group is selected from an aromatic group or a fused aromatic group having a carbon atom number of 6 to 18;
adding tri-tert-butyl phosphine into the first reaction vessel dropwise, and heating to reflux.

2. The production process according to claim 1, wherein the first organic solvent is toluene.

3. The production process according to claim 1, wherein the dibenzoanthracene bromide containing $R_1$ group is produced by the steps of:
adding 1.2,5.6-di(2-bromo)benzo(9,10-dicarbonyl)anthracene and a second organic solvent into a second reaction vessel;
after 1.2,5.6-di(2-bromo)benzo(9,10-dicarbonyl)anthracene is dissolved into the second organic solvent, reducing the temperature of the second reaction vessel; adding butyl lithium into the second reaction vessel dropwise; after a second predetermined time, adding a solution of an iodide having a $R_1$ group into the second reaction vessel; raising the temperature of the second reaction vessel to normal temperature for reaction for a third predetermined time, so as to obtain an alcohol of a dibenzoanthracene bromide containing a $R_1$ group;
adding the alcohol of the dibenzoanthracene bromide containing a $R_1$ group, potassium iodide, sodium dihydrogen phosphate and a third organic solvent into a third reaction vessel;
heating to reflux for a fourth predetermined time, and then cooling to room temperature;
obtaining the dibenzoanthracene bromide containing a $R_1$ group.

4. The production process according to claim 3, wherein the second organic solvent is tetrahydrofuran.

5. The production process according to claim 3, wherein the third organic solvent is glacial acetic acid.

6. The production process according to claim 3, wherein the 1.2,5.6-di(2-bromo)benzo(9,10-dicarbonyl)anthracene is produced by the steps of:
adding 7-bromonaphthofuran-1,3-dione and 2-iodonaphthalene into a fourth reaction vessel and heating the fourth reaction vessel;
adding aluminium trichloride into the fourth reaction vessel; performing reaction until no more hydrogen chloride is discharged; when the fourth reaction vessel is cooled, slowly pouring the solution in the fourth reaction vessel into an ice water solution of sodium hydroxide, so as to obtain (6-bromo-1-(6-bromo-2-naphthoyl)-2-naphthoyl)aluminum dichloride;
adding (6-bromo-1-(6-bromo-2-naphthoyl)-2-naphthoyl) aluminum dichloride and concentrated sulfuric acid into a fifth reaction vessel and heating the fifth reaction vessel.

7. The production process according to claim 1, wherein $R_2$ group is selected from an aromatic amine group.

8. The production process according to claim 1, wherein $R_2$ group is selected from an aromatic amine group having a carbon atom number of 6 to 30.

9. The production process according to claim 1, wherein said $R_1$ group is phenyl, 9-phenanthryl, p-tolyl, 4-biphenyl, or 2-naphthyl.

10. The production process according to claim 1, wherein said $R_2$ group is diphenylamino, N-phenyl-4-biphenylamino, di(4-biphenyl)amino, N-phenyl-2-naphthylamino, 2,2-dinaphthylamino, or N-phenyl-3,5-diphenyl phenylamino.

* * * * *